(12) United States Patent
Nakazawa et al.

(10) Patent No.: US 8,835,130 B2
(45) Date of Patent: Sep. 16, 2014

(54) TISSUE ARRAY PRODUCTION METHOD

(75) Inventors: Yoshiaki Nakazawa, Chikuma (JP);
Masaki Takano, Chikuma (JP);
Masahiko Arakawa, Chikuma (JP);
Kohji Naritake, Chikuma (JP)

(73) Assignees: Sakura Seiki Co., Ltd., Nagano (JP);
Sakura Finetek Japan Co., Ltd., Tokyo (JP)

( * ) Notice: Subject to any disclaimer, the term of this patent is extended or adjusted under 35 U.S.C. 154(b) by 0 days.

(21) Appl. No.: 13/810,662

(22) PCT Filed: Jul. 26, 2011

(86) PCT No.: PCT/JP2011/066976
§ 371 (c)(1),
(2), (4) Date: Jan. 16, 2013

(87) PCT Pub. No.: WO2012/014897
PCT Pub. Date: Feb. 2, 2012

(65) Prior Publication Data
US 2013/0115652 A1    May 9, 2013

(30) Foreign Application Priority Data
Jul. 29, 2010   (JP) ................................ 2010-170958

(51) Int. Cl.
*C12N 5/00*    (2006.01)
*G01N 33/48*   (2006.01)
*G01N 1/06*    (2006.01)
*G01N 1/36*    (2006.01)

(52) U.S. Cl.
CPC .. *G01N 1/36* (2013.01); *G01N 1/06* (2013.01); *G01N 2001/362* (2013.01); *G01N 2001/368* (2013.01)
USPC ........................................ 435/40.5; 435/325

(58) Field of Classification Search
None
See application file for complete search history.

(56) References Cited

U.S. PATENT DOCUMENTS

| 7,029,615 B2 | 4/2006 | Lilischkis et al. | |
| 2010/0087333 A1* | 4/2010 | Fukuoka | 506/13 |

FOREIGN PATENT DOCUMENTS

| JP | 10293095 | 11/1998 | |
| JP | 2004/258017 A * | 9/2004 | .............. G01N 1/36 |
| JP | 2004258017 | 9/2004 | |
| WO | WO-2007109639 | 9/2007 | |
| WO | WO-2008/108410 A1 * | 9/2008 | .............. C12Q 1/24 |
| WO | WO-2008108410 | 12/2008 | |
| WO | WO-2010027012 | 3/2010 | |

OTHER PUBLICATIONS

Yasuhiko, K.JP2004-258017A.Array block preparation method, tissue scooping-out device used for the same and tissue block.MT English translation.pp. 1-23. specif. p. 9.*
Sakura Seiki Co., Ltd., et al., International Search Report for PCT/JP2011/066976 dated Sep. 20, 2011.

* cited by examiner

*Primary Examiner* — John S Brusca
*Assistant Examiner* — Sharon M Papciak
(74) *Attorney, Agent, or Firm* — Blakely Sokoloff Taylor & Zafman LLP

(57) ABSTRACT

Tissue array production method enables even roll-shaped tissue pieces having various diameters to be steadily fixed to a substrate block is provided. In a method in which roll-shaped tissue pieces formed by rolling sheet-like tissue pieces in the shape of a roll are arranged on a substrate in an array form, a tissue array is produced by placing a holding member which holds a plurality of roll-shaped tissue pieces so that their axis directions are vertically directed in a container into which a melted embedding medium is poured for its accumulation, to hold the respective roll-shaped tissue pieces in the holding member; pouring the embedding medium into the container, to form a substrate block constituted so that the plurality of roll-shaped tissue pieces is arranged in the array form; and slicing the substrate block so that the roll-shaped tissue pieces are ring-shaped.

6 Claims, 4 Drawing Sheets

TISSUE ARRAY PRODUCTION METHOD

CROSS-REFERENCE to RELATED APPLICATION

This is a non-provisional application claiming the benefit of International Patent Application No. PCT/JP2011/066976, filed Jul. 26, 2011.

TECHNICAL FIELD

The present invention relates to a method for producing a tissue array obtained by arranging tissue pieces on a substrate in an array form, and particularly to a method for producing a tissue array by using roll-shaped tissue pieces constituted by rolling the tissue pieces in the shape of a roll.

BACKGROUND ART

For test and analysis of body tissues, a tissue array constituted by arranging a plurality of tissue pieces on a substrate is used. The tissue array is used for testing of the presence or absence of lesional tissues, analysis and screening of genes and proteins, etc. by coating or the like of a staining solution which specifically stains test article, or the like.

In relation to formation of tissue pieces constituting the tissue array, it has been general to punch a tissue block embedded with an embedding medium such as paraffin and to circularly cut out the tissue block for sampling a core.

However, according to such a method for forming the tissue pieces, there have been problems in which a particular region of interest which especially attracts attention in the lesional tissue in the tissue block may be deleted when it is sliced after sampling of the core.

Furthermore, among researchers who study body tissues, some researchers think that punching the tissue block is undesirable for the subsequent researches because the region is completely deleted from the tissue block.

Therefore, there has been examined the formation of the tissue pieces constituting the tissue array, not by the method of cutting out the circular core from the tissue block, but by another method.

Methods proposed in order to solve the above-mentioned problems are disclosed in Patent Literatures 1 and 2.

In the methods for forming tissue pieces disclosed in Patent Literatures 1 and 2, a tissue block is first sliced by a microtome or the like and a sheet-like tissue piece is obtained. Subsequently the sheet-like tissue piece is rolled up.

The rolled-up roll-shaped tissue piece is inserted into a hole of the substrate block obtained by forming an embedding medium such as paraffin into a block shape. When a predetermined number of roll-shaped tissue pieces are arranged on the substrate block, the substrate block is sliced so that the roll-shaped tissue pieces are in the form of round slices, and the slices are placed on the substrate such as a microscope slide, for the formation of a tissue array.

In addition, when the roll-shaped tissue piece is inserted into the hole of the substrate block constituted by forming the embedding medium such as paraffin into the block shape, the diameter of the roll-shaped tissue piece preferably coincides with that of the hole. This is because positioning can be securely performed by making these diameters coincide with each other.

In this way, in the formation methods described in Patent Literatures 1 and 2, various regions in a wide range of tissues can be put into one tissue piece by rolling the sheet-like tissue piece in the shape of a roll, and thus the problem of deleting the particular region of interest which especially attracts attention in the lesional tissue can be solved.

Consequently, the tissue can remain only by thinly slicing its surface without punching the tissue block and can be useful for subsequent studies.

PRIOR ART DOCUMENTS

Patent Documents

PTL 1: WO 2010/027012, the brochure
PTL 2: WO 2008/108410, the brochure

DISCLOSURE OF THE INVENTION

Problems to be Solved

As mentioned above, in the methods described in Patent Literatures 1 and 2, formed roll-shaped tissue pieces are inserted into the holes of the substrate block constituted by forming the embedding medium such as paraffin into the block shape.

However, the diameters of the roll-shaped tissue pieces vary depending on the sizes and thicknesses of the tissue pieces. Thus, there are problems in which even if a hole having a prescribed diameter is formed on the substrate block, the roll-shaped tissue piece cannot be inserted into the hole in the case of a roll-shaped tissue piece with a larger diameter than the hole, and a position cannot be steadily fixed due to movement of the roll-shaped tissue piece in the hole in the case of a roll-shaped tissue piece with a smaller diameter than the hole.

Therefore, the present invention has been made to solve the above-mentioned problems, and its object is to provide a tissue array production method which enables even roll-shaped tissue pieces having various diameters to be steadily fixed to the substrate block.

Solutions to be Solved

According to the tissue array production method related to the present invention, wherein the tissue array is produced in which the roll-shaped tissue pieces formed by rolling sheet-like tissue pieces in the shape of a roll are arranged on the substrate in an array form, the tissue array production method is characterized by placing a holding member which holds a plurality of roll-shaped tissue pieces so that their axis directions are vertically directed in a container into which a melted embedding medium is poured for accumulation, to hold each roll tissue piece in the holding member; pouring the embedding medium into the container, to form the substrate block constituted so that the plurality of roll tissue pieces is arranged in an array form; and slicing the substrate block so that the roll-shaped tissue piece is ring-shaped, to place the sliced piece on the substrate.

According to this method, the plurality of roll-shaped tissue pieces can be held and their circumferences can be embedded with the melted embedding medium to produce the substrate block, and thereby the tissue array in which the plurality of roll-shaped tissue pieces is steadily arranged can be produced.

The holding member may be characterized by using an elastic member, in which a plurality of insertion holes having at least the same diameters as the minimum diameter of the roll-shaped tissue piece is formed, to hold the outer periphery of the roll-shaped tissue piece. According to this method, even if each roll-shaped tissue piece has a different diameter, the insertion holes in the elastic member can hold every roll-shaped tissue piece.

In addition, the insertion hole may be characteristically polygon.

In other words, since the cross-section of the roll-shaped tissue piece is approximately circular, the tissue piece may be hardly held by a holding strength of the elastic member due to the circular cross-section of the insertion hole, but a polygonal shape can ensure holding of the roll-shaped tissue piece with a circular cross-section. In addition, the polygonal cross-section of the insertion hole is able to decrease the contact area between the roll-shaped tissue piece and the elastic member, to further facilitate enlargement of the diameter of the insertion hole by reducing elasticity, and to increase the allowance for uneven diameters of the roll-shaped tissue pieces.

In addition, the holding member may be characterized by using a grid-like member including a plurality of grid squares with at least the same side length as the least diameter of the roll-shaped tissue piece to hold the outer periphery of the roll-shaped tissue piece.

According to this method, even if each roll-shaped tissue piece has a different diameter, every roll-shaped tissue piece can be held by elastic deformation of each side of the grid-like member.

Furthermore, this method may be characterized in that bar-like holding members to be inserted into the axial cores of the plurality of roll-shaped tissue pieces are used as the holding member, to hold the axial cores of the roll-shaped tissue pieces.

According to this method, even if each roll-shaped tissue piece has a different diameter, every roll-shaped tissue piece can be held.

Effects of the Invention

According to the tissue array production method of the present invention, even if the roll-shaped tissue pieces have different diameters, they can be steadily fixed on the substrate block, and the tissue array can be securely produced.

EMBODIMENTS OF THE INVENTION

Figure 1:
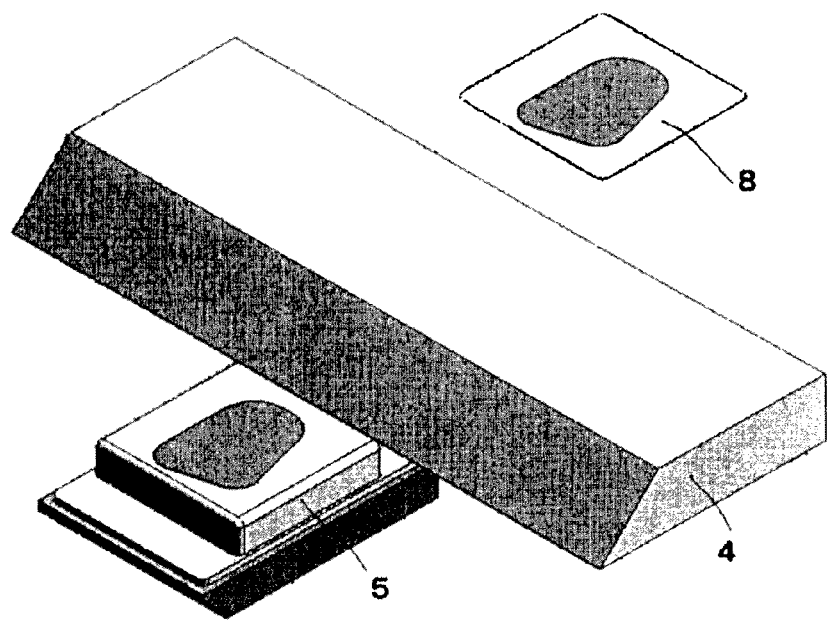
FIG. 1 illustrates an explanatory drawing of cutting out of the sheet-like tissue piece.

Hereinafter, the tissue array production method related to the embodiment will be explained on the basis of the drawings. First, the roll-shaped tissue piece used for the tissue array will be explained on the basis of FIG. 1 to FIG. 2.

A roll-shaped tissue piece 6 is constituted by rolling the sheet-like tissue piece in the shape of a roll.

As simple explanation on its production method, a tissue block 5 embedded with the embedding medium such as paraffin is cut into a sheet with a thickness of approximately 100 µm by a microtome 4 to form a sheet-like tissue piece 8. Then, the sheet-like tissue piece 8 is wound around a core rod 11 to be formed as the roll-shaped tissue piece 6. Winding should be conducted while heating so as to allow secure rolling.

Figure 2:
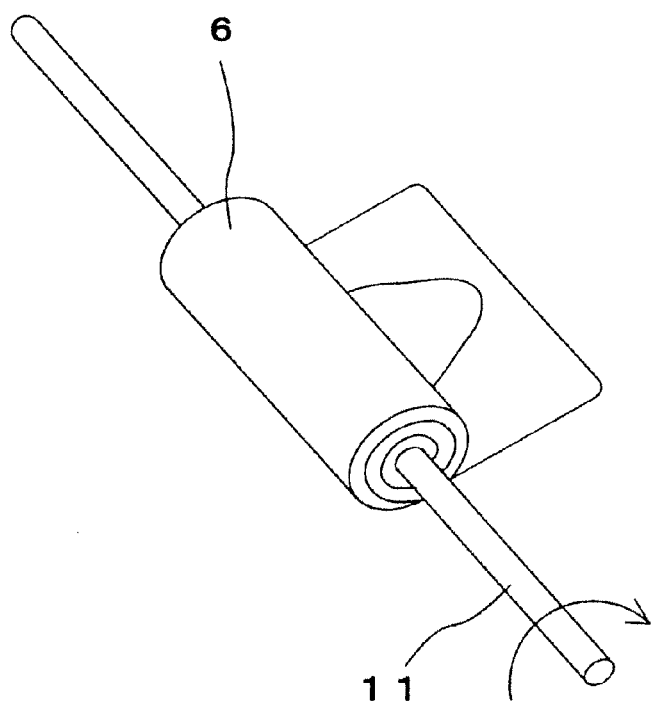
FIG. 2 illustrates an explanatory drawing of a state during winding of the sheet-like tissue piece around the core rod.
Figure 3:
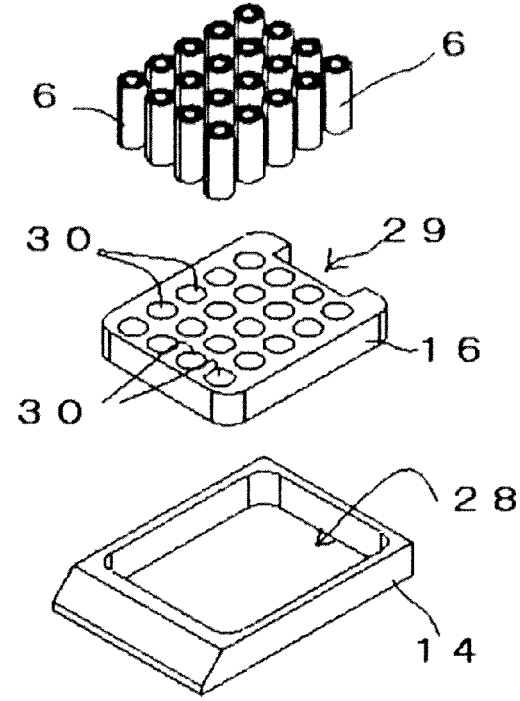
FIG. 3 illustrates an exploded view of a configuration for arranging the roll-shaped tissue pieces in a first embodiment.
Figure 3:
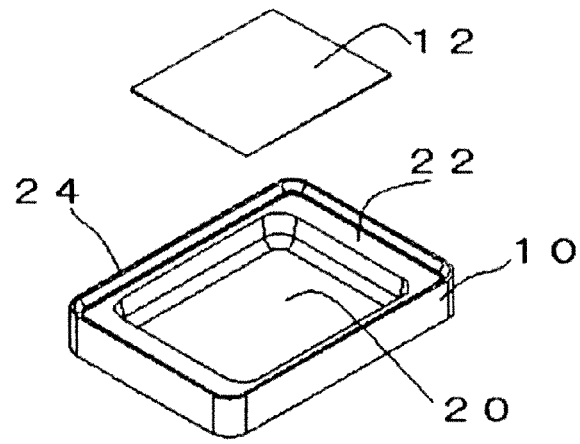

In addition, the core rod 11 shown in FIG. 2 may be pulled out after the tissue piece is rolled.

(The First Embodiment)

Subsequently, the first embodiment of the tissue array production method by using the roll-shaped tissue piece mentioned above will be explained on the basis of FIG. 3 to FIG. 6.

The plurality of roll-shaped tissue pieces 6 is arranged in a container formed in a form that allows accumulation of the melted embedding medium (paraffin in the embodiment). An embedding dish 10 which embeds the tissue piece for producing a pathological specimen and an embedding frame 14 can be used as a container.

Hereinafter, the embodiment using the embedding dish 10 and the embedding frame 14 will be explained.

In the embedding dish 10, an accumulation part 20 which is concave in the center and can accumulate the melted paraffin is formed. Around the accumulation part 20, there is formed an embedding frame-placing part 22 which is a step formed outward from the upper end of the accumulation part 20 and which has an upper face formed in a plane shape. Around the embedding frame-placing part 22, there is formed a wall 24, the out side of which is formed on the same plane as the outer wall surface, and which projects upward so as to cover the lateral face of the embedding frame 14 placed on the embedding frame-placing part 22.

The embedding frame 14 is placed on the embedding frame-placing part 22 of the embedding dish 10 and used integrally with the embedding dish 10.

In the center of the embedding frame 14, a communication hole 28 having a shape the same as or smaller than that in a planar view of the accumulation part 20 of the embedding dish 10 is formed. When an embedding frame 14 is placed on the embedding dish 10, the accumulation part 20 of the embedding dish 10 communicates with the communication hole 28 of the embedding frame 14, to form a deep accumulation part.

In the embodiment, the plurality of roll-shaped tissue pieces 6 is held by a holding member 16 made of an elastic body. As the elastic body, a material such as a sponge and a rubber can be used.

The holding member 16 is formed so that its size is a dimension that makes it possible to fit the holding members just into the communication hole 28 of the embedding frame 14, and its thickness is nearly the same as the length in the top-to-bottom direction of the communication hole 28 of the embedding frame 14.

In addition, although a shape in a planar view of the holding member 16 is nearly the same as a shape in a planar view of the communication hole 28 of the embedding frame 14, a cut-out portion 29 is partially formed therein. The melted paraffin can be poured from the cut-out portion 29.

In the holding member 16, a plurality of insertion holes for holding the roll-shaped tissue piece 6 are formed through the thickness direction (top-to-bottom direction) of the 16.

The diameter of the insertion hole 30 is set to be somewhat smaller than the predicted minimum diameter of the roll-shaped tissue piece 6. Thus, even in the case of the thinnest roll-shaped tissue piece 6, the roll-shaped tissue piece 6 inserted into the insertion hole 30 broadens the insertion hole 30, and the holding member 16 is elastically deformed. A restoring force of this elastic deformation can ensure holding of the outer periphery of the roll-shaped tissue piece 6 by the inner wall of the insertion hole 30, to fix it to the accumulation part 20 of the embedding dish 10.

In addition, the cross-section of the insertion hole 30 of the holding member 16 may be formed into not a circular shape but a polygonal shape. That is, as compared with the case of a circular cross-section of the insertion hole 30, if there are corners in the inner wall surface of the insertion hole 30, the corners can enhance a fixation function by reliably pressing the outer periphery of the roll-shaped tissue piece 6. In addition, the polygonal cross-section of the insertion hole 30 can decrease the contact area between the roll-shaped tissue piece 6 and the elastic member, further facilitate broadening of the diameter of the insertion hole 30 by reducing the elasticity, and increase the allowance for uneven diameters of the roll-shaped tissue pieces 6.

A double-stick tape 12 may be located on the inner bottom face of the accumulation part 20 of the embedding dish 10. One face (lower face) of the double-stick tape 12 adheres for fixation to the inner bottom face of the accumulation part 20, and another face (upper face) adheres to the lower end faces of the plurality of roll-shaped tissue pieces 6 held by the holding member 16.

In this way, the lower end faces of the plurality of roll-shaped tissue pieces 6 can be uniformed on the same plane by fixation through adhesion of the lower end faces of the plurality of roll-shaped tissue pieces 6, to the double-stick tape 12. Thereby, the roll-shaped tissue pieces 6 can be stably arranged.

In addition, even if the double-stick tape 12 is not used, the upper end faces of the roll-shaped tissue pieces 6 held by the holding member 16 are pushed, and thereby the roll-shaped tissue pieces 6 can be stably arranged by bringing the lower end faces of the roll-shaped tissue pieces 6 into contact with the inner bottom face of the accumulation part 20 of the embedding dish 10.

Subsequently, procedures for producing the tissue array by using the above-mentioned instruments will be explained.

First, the double-stick tape 12 is placed on the inner bottom face of the accumulation part 20 of the embedding dish 10.

The roll-shaped tissue pieces 6 are inserted into each insertion hole 30 of the holding member 16. Incidentally, each roll-shaped tissue piece 6 is previously cut with uniformity so that the length of the roll-shaped tissue piece 6 to be inserted is the same as the length from the inner bottom face of the accumulation part 20 of the embedding dish 10 to the upper face of the holding member 16 attached to the communication hole 28 of the embedding frame 14. In addition, the length of each roll-shaped tissue piece 6 may be uniformly cut after formation of a substrate block 40.

Additionally, the holding member 16 holding the plurality of roll-shaped tissue pieces 6 is attached to the communication hole 28 of the embedding frame 14. At this time, the embedding frame 14 is preferably fixed to the holding member 16 with an adhesive or the like.

The embedding frame 14 to which the holding member 16 is attached is placed on the embedding frame-placing part 22 of the embedding dish 10.

Figure 4:
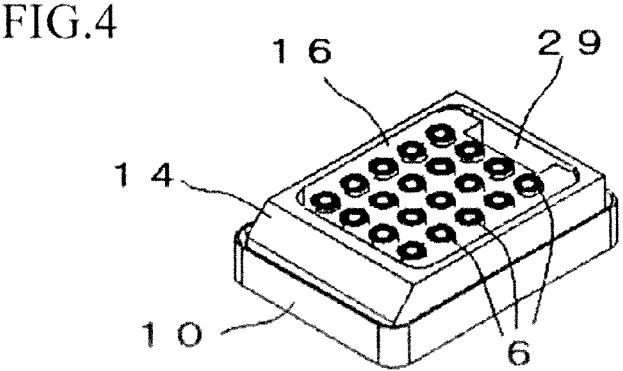
FIG. 4 illustrates an explanatory drawing of a configuration for arranging the roll-shaped tissue pieces in the first embodiment.
Figure 5:
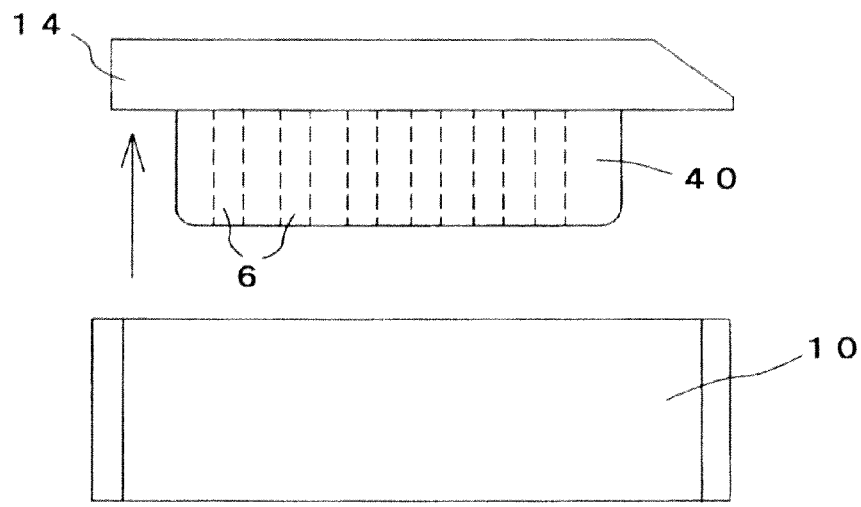
FIG. 5 illustrates an explanatory drawing of the substrate block produced by the constitution of FIG. 4.

This state is shown in FIG. 4.

The melted paraffin is poured into the accumulation part 20 of the embedding dish 10 in a state where the plurality of roll-shaped tissue pieces 6 is held by the holding member 16. In relation to an inlet, the paraffin is preferably poured from the cut-out portion 29 of the holding member 16.

Subsequently, the melted paraffin is cooled until it is solidified.

When the melted paraffin is solidified, the substrate block 40 in which the plurality of roll-shaped tissue pieces 6 is arranged and embedded in the paraffin is completed. In FIG. 5A, a state where the substrate block 40 is pulled out together with the embedding frame 14 from the embedding dish 10 is shown.

The substrate block 40 is preferably treated integrally with the embedding frame 14. That is, the embedding frame 14 is detached from the embedding dish 10, and the substrate block including the embedding frame 14 is also treated as the substrate block 40.

Since the embedding frame 14 also includes an area on which notes or the like is described, descriptions of information of the substrate block 40 are useful for subsequent researches or the like, and mix-up or the like can also be prevented. Furthermore, when the substrate block 40 is thinly cut (sliced) by the microtome or the like, the embedding frame 14 has only to be fixed by any fixing means for fixing the tissue block, and thereby slices can be easily produced from the substrate block 40.

Figure 6:
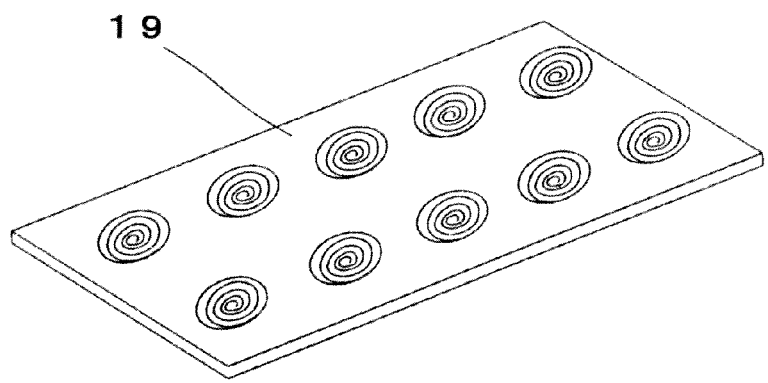
FIG. 6 illustrates a perspective view of a tissue array sheet.

As shown in FIG. 6, a sheet-like object obtained by slicing the substrate block 40 is a tissue array sheet 19. Then, the tissue array is produced by placing the tissue array sheet 19 on the substrate (not shown). Note that various substrates such as a microscope slide, a nylon film substrate or a silicon substrate can be used as the substrate.

Figure 7:
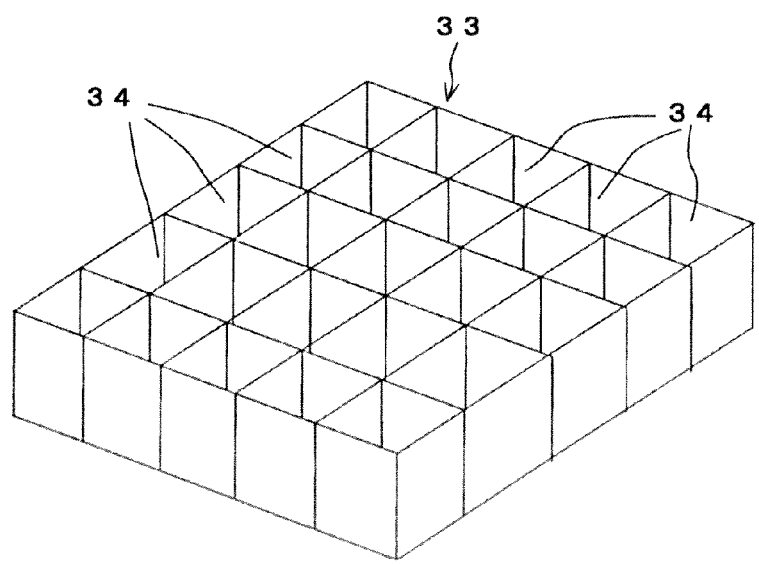
FIG. 7 illustrates an explanatory drawing of another example of the holding member in the first embodiment.

Meanwhile, another example of the holding member in the embodiment will be explained on the basis of FIG. 7.

As the holding member 33, there is used a grid-like member in which a plurality of grid squares 34 with somewhat shorter side length than the predicted least diameter of the roll-shaped tissue piece 6 is formed.

The size of the holding member 33 is a dimension that makes it possible to just fit the member into the communication hole 28 of the embedding frame 14, and its thickness is formed so as to be nearly the same as the top-to-bottom length of the communication hole 28 of the embedding frame 14.

The grid-like member can be formed by interlocking a plurality of elastically deformable plate-like members in a grid arrangement.

This holding member 33 enables the roll-shaped tissue pieces 6 to be held in each grid square 34. Furthermore, this holding member 33 is used by being attached to the communication hole 28 of the embedding frame 14. At this time, the embedding frame 14 is preferably fixed to the holding member 33 with an adhesive or the like.

(The Second Embodiment)

Figure 8:
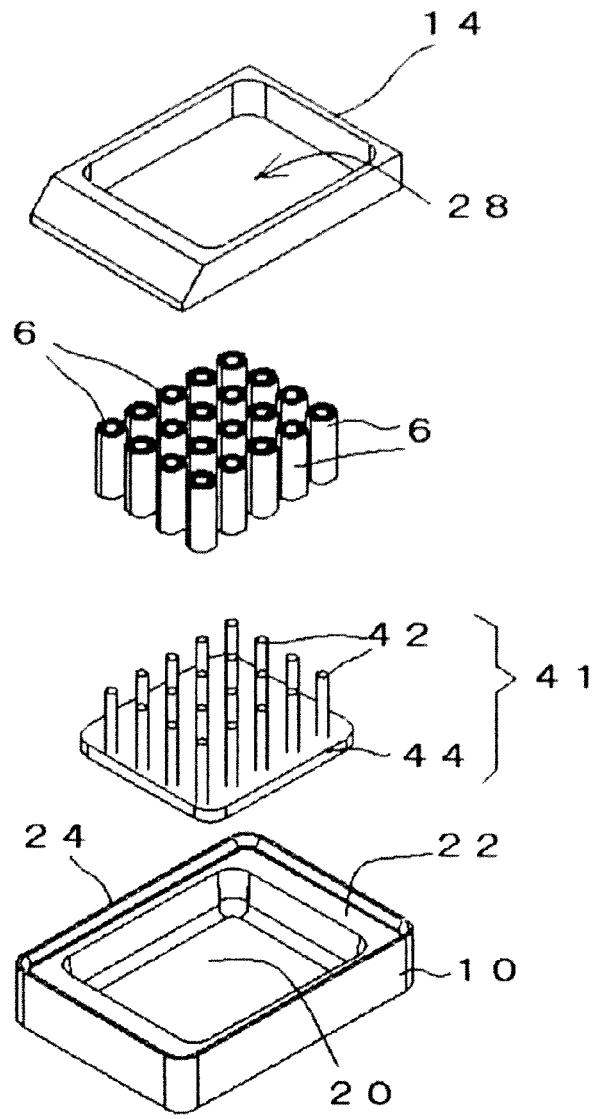
FIG. 8 illustrates an exploded view of a configuration for arranging the roll-shaped tissue pieces in a second embodiment.

Subsequently, the second embodiment of the tissue array production method using the roll-shaped tissue piece will be explained on the basis of FIG. 8 to FIG. 9.

Note that the same constituents as those explained in the above-mentioned embodiment are given the same reference numerals, and their explanations may be omitted.

A holding member 41 in the embodiment includes a plurality of bar-like members 42 which are inserted into the axial core parts of the roll-shaped tissue pieces 6 and hold the axial core parts of the roll-shaped tissue pieces 6. When the core rod 11 is pulled out at the time of forming the roll-shaped tissue piece 6, a hollow cavity is formed in the axial core part of the roll-shaped tissue piece 6, into which the bar-like member 42 can be inserted. Furthermore, even in a case where the core rod 11 is not pulled out, if the core rod 11 is formed in a cylindrical shape, the bar-like member 42 can be inserted into this cylindrical inner space.

The plurality of bar-like members 42 is positioned projecting upward on the upper face of a base 44, and the base 44 is formed into the size in which the base can be positioned on the inner bottom face of the accumulation part 20 of the embedding dish 10.

Note that the tip of the bar-like member 42 of the holding member 41 may be sharpened.

Subsequently, procedures for producing the tissue array in the second embodiment will be explained. First, the holding member 41 is positioned on the inner bottom face of the accumulation part 20 of the embedding dish 10.

The bar-like member 42 of the holding member 41 is inserted into the axial core part of the roll-shaped tissue piece 6, and the plurality of roll-shaped tissue pieces 6 is arranged in the embedding dish 10 and is fixed. Incidentally, each roll-shaped tissue piece 6 is previously cut with uniformity so that the length of the roll-shaped tissue piece 6 to be inserted is the same as the length from the inner bottom face of the accumulation part 20 of the embedding dish 10 to the upper face of the embedding frame 14. In addition, the length of each roll-shaped tissue piece 6 may be uniformly cut after formation of the substrate block 40.

Then the embedding frame 14 is placed on the embedding frame-placing part 22 of the embedding dish 10.

Figure 9:
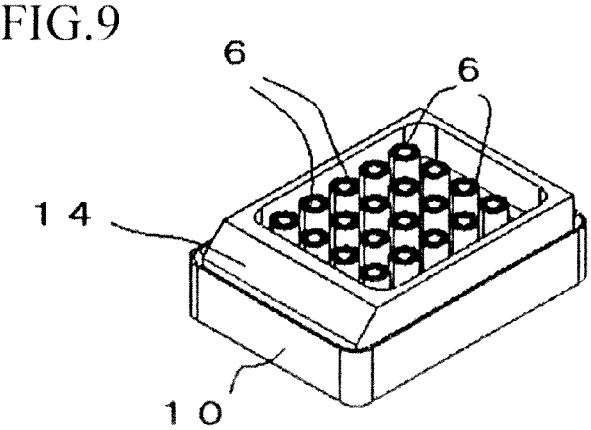
FIG. 9 illustrates an explanatory drawing of a configuration for arranging the roll-shaped tissue pieces in the second embodiment.

This state is shown in FIG. 9.

The melted paraffin is poured into the accumulation part 20 of the embedding dish 10 in a state where the plurality of roll-shaped tissue pieces 6 is held by the holding member 41. The melted paraffin is poured from a gap among the respective roll-shaped tissue pieces 6 in the communication hole 28 of the embedding frame 14.

Subsequently, the melted paraffin is cooled until it is solidified.

Note that, when the melted paraffin is solidified, the substrate block 40 in which the plurality of roll-shaped tissue pieces 6 is arranged and embedded in the paraffin is completed, but the process for slicing the substrate block 40 to produce the tissue array is the same as that in the first embodiment, and therefore this explanation is omitted herein.

Note that, although the embedding medium used in the embodiment is exemplified by a paraffin, the embedding mediums include a non-hydrophilic embedding medium such as celloidin, a polyester resin, a polyamide resin, and a (meth) acrylic acid resin, a hydrophilic embedding medium such as carbowax and gelatin, and an embedding medium having a combination of two or more of them.

Preferable embedding mediums include paraffins such as a paraffin and a paraffin containing an additive of a synthetic polymer such as polyethylene.

According to the present invention, the roll-shaped tissue piece can be steadily fixed to the substrate block to ensure production of the tissue array, both in the method for holding the outer periphery of the roll-shaped tissue piece 6 in the first embodiment as mentioned above, and in the method for holding the axial core part of the roll-shaped tissue piece 6 in the second embodiment.

What is claimed is:

1. A tissue array production method, wherein roll-shaped tissue pieces formed by rolling sheet-like tissue pieces in the shape of a roll are arranged on a substrate in an array form, the method comprising:
    placing a holding member which holds a plurality of roll-shaped tissue pieces so that their axis directions are vertically directed in a container into which a melted embedding medium is poured for its accumulation, to hold the respective plurality of roll-shaped tissue pieces in the holding member;
    pouring the embedding medium into the container to form a substrate block constituted so that the plurality of roll-shaped tissue pieces is arranged in the array form; and
    slicing the substrate block so that the plurality of roll-shaped tissue pieces are ring-shaped,
    wherein the holding member comprises an elastic member including a plurality of insertion holes each having at least the same diameter as the minimum diameter of ones of the roll-shaped tissue pieces to respectively hold the outer periphery of ones of the plurality of roll-shaped tissue pieces.

2. The tissue array production method according to claim 1, wherein each of said plurality of insertion holes has a polygonal shape.

3. A tissue array production method, wherein roll-shaped tissue pieces formed by rolling sheet-like tissue pieces in the shape of a roll are arranged on a substrate in an array form, the method comprising:
    placing a holding member which holds a plurality of roll-shaped tissue pieces so that their axis directions are vertically directed in a container into which a melted embedding medium is poured for its accumulation, to hold the respective plurality of roll-shaped tissue pieces in the holding member;
    pouring the embedding medium into the container to form a substrate block constituted so that the plurality of roll-shaped tissue pieces is arranged in the array form; and
    slicing the substrate block so that the plurality of roll-shaped tissue pieces are ring-shaped,
    wherein the holding member comprises a plurality of bar-like members projecting from a base, said bar-like members operable to be inserted into respective ones of the axial cores of the plurality of roll-shaped tissue pieces.

4. The tissue array production method according to claim 1, wherein the embedding medium is a paraffin.

5. The tissue array production method according to claim 4, wherein each of said plurality of said insertion holes has a polygonal shape.

6. The tissue array production method according to claim 3, wherein the embedding medium is a paraffin.

* * * * *